United States Patent [19]
Furuya et al.

[11] Patent Number: 5,159,380
[45] Date of Patent: Oct. 27, 1992

[54] PHOTOGRAPHING LIGHT QUANTITY CONTROLLER FOR ENDOSCOPE

[75] Inventors: Katsuhiko Furuya; Masaaki Nakasima; Takayuki Enomoto; Tadashi Takahashi, all of Tokyo, Japan

[73] Assignee: Asahi Kogaku Kogyo Kabushiki Kaisha, Tokyo, Japan

[21] Appl. No.: 728,520

[22] Filed: Jul. 11, 1991

[30] Foreign Application Priority Data

Jul. 26, 1990 [JP] Japan .................................. 2-200054

[51] Int. Cl.⁵ .......................... G03B 15/05; A61B 1/06
[52] U.S. Cl. ..................................... 354/415; 354/416; 354/62; 128/6; 315/241 P
[58] Field of Search ................ 354/62, 415, 416, 417, 354/420, 413, 145.1, 422; 362/4, 5; 128/6; 315/241 P, 151, 159

[56] References Cited

U.S. PATENT DOCUMENTS

| | | | |
|---|---|---|---|
| 3,680,457 | 8/1972 | Uno et al. | 354/415 |
| 4,021,663 | 5/1977 | Takahashi | 128/4 X |
| 4,086,583 | 4/1978 | Takahashi | 354/62 |
| 4,297,011 | 10/1981 | Adams, Jr. | 354/416 |
| 4,322,129 | 3/1982 | Takahashi et al. | |
| 4,329,623 | 5/1982 | Hattori | 315/151 |
| 4,366,529 | 12/1982 | Takahashi et al. | 362/4 |
| 4,398,127 | 8/1983 | Bahn et al. | 315/151 |
| 4,509,508 | 4/1985 | Tsukaya | 128/6 |
| 4,985,725 | 1/1991 | Serikawa | 354/416 |

FOREIGN PATENT DOCUMENTS

| | | |
|---|---|---|
| 53-36980 | 4/1978 | Japan . |
| 57-26127 | 6/1982 | Japan . |
| 58-75526 | 5/1983 | Japan . |
| 58-94829 | 6/1983 | Japan . |
| 58-97355 | 6/1983 | Japan . |
| 60-51896 | 11/1985 | Japan . |
| 61-13236 | 1/1986 | Japan . |
| 61-36928 | 8/1986 | Japan . |
| 2-84609 | 3/1990 | Japan . |

*Primary Examiner*—W. B. Perkey
*Attorney, Agent, or Firm*—Sandler, Greenblum and Bernstein

[57] ABSTRACT

A photographing light quantity controller for an endoscope, which is used to control the quantity of illuminating light when a photograph is to be taken through the endoscope. The photographing light quantity controller comprises a device for supplying light for illuminating an object to be viewed by the endoscope, a photoelectric conversion device for converting into an electric signal, a brightness level of exposure light that is applied to a photographic plane in a photographing device after being reflected from the object, and a device for integrating the output from the photoelectric conversion device and outputting the resulting integral value. The photographing light quantity controller further comprises a device for outputting a numerical value corresponding to a quantity of exposure light which is to be applied to the photographic plane, a device for converting the integral value into a numerical value on the same scale as that of the numerical value of the exposure quantity, and a device for deciding an exposure quantity, and a device for deciding an exposure time by comparing the numerical value of the exposure quantity and the output value from the integral value converting device.

13 Claims, 11 Drawing Sheets

FIG.3A

| EXPOSURE QUANTITY (RELATIVE VALUE) | $2^{-4}$ | $2^{-3}$ | $2^{-2}$ | $2^{-1}$ | 1 | $2^1$ | $2^2$ | $2^3$ | $2^4$ |
|---|---|---|---|---|---|---|---|---|---|
| CONVERTED EXPOSURE QUANTITY $V_I$ | 8 | 16 | 32 | 64 | 128 | 256 | 512 | 1024 | 2048 |
| CONVENTIONAL REFERENCE VOLTAGE $V_R$ [VOLT] | 0.063 | 0.13 | 0.25 | 0.50 | 1.0 | 2.0 | 4.0 | 8.0 | 16 |

FIG.3B

| EXPOSURE QUANTITY (RELATIVE VALUE) | $2^{-4}$ | $2^{-3}$ | $2^{-2}$ | $2^{-1}$ | 1 | $2^1$ | $2^2$ | $2^3$ | $2^4$ |
|---|---|---|---|---|---|---|---|---|---|
| EXPOSURE INDEX | 18 | 16 | 14 | 12 | 10 | 8 | 6 | 4 | 2 |
| CONVERTED EXPOSURE QUANTITY $V_I$ | 8 | 16 | 32 | 64 | 128 | 256 | 512 | 1024 | 2048 |

PHOTOGRAPHING LIGHT QUANTITY CONTROLLER FOR ENDOSCOPE

BACKGROUND OF THE INVENTION

The present disclosure relates to subject matter contained in Japanese Patent application No. 2-200054 (filed on Jul. 26, 1990), which is expressly incorporated herein by reference in its entirety.

FIELD OF THE INVENTION

The present invention relates to a photographing light quantity controller for an endoscope, which is used to control the quantity of illuminating light when a photograph is to be taken through the endoscope.

Endoscopes are generally designed to be capable of not only observing the inside of a hollow organ in the patient's body but also taking a photograph of it.

DESCRIPTION OF THE PRIOR ART

In a conventional photographing light quantity controller for an endoscope, reflected light from an object that is illuminated by a light source is received and converted into an electric signal with a light-receiving element. The output of the light-receiving element is integrated to obtain an integral value. When the integral value reaches a preset reference voltage, the application of the illuminating light to the object is stopped, thus effecting automatic control of the quantity of photographing light.

To take a photograph through an endoscope, however, it is necessary to enable photographing to be effected over a wide range of light exposure so that an optimum quantity of photographing light is obtained in conformity with the kind of endoscope used, the condition of a part which is photographed, and so forth. For this purpose, it is necessary to enlarge the range within which the reference voltage can be set. More specifically, the reference voltage must be capable of being set in a wide range, from a very low voltage to a high voltage, e.g., from 50 mV to 10V.

In order to enable the reference voltage to be set in such a wide range, however, hardware for generating a high voltage is needed only for producing a reference voltage. In addition, since the S/N ratio becomes low when a very low voltage is set as a reference voltage, hardware for coping with this problem is also needed. Consequently, the scale of the system enlarges, and the cost of the product increases.

SUMMARY OF THE INVENTION

An object of the present invention is to provide a photographing light quantity controller for an endoscope, which is capable of coping with a wide range of photographing conditions (i.e., light exposure) with simple and inexpensive hardware.

Other objects and advantages of the present invention will become apparent from the following detailed description of an illustrated embodiment of the invention.

According to the present invention, there is provided a photographing light quantity controller for an endoscope, which is used to control the quantity of illuminating light when a photograph is to be taken through the endoscope, comprising: a device for supplying light for illuminating an object to be viewed by the endoscope; a photoelectric conversion device for converting into an electric signal, a brightness level of exposure light that is applied to a photographic plane in a photographing device after being reflected from the object; a device for integrating the output from the photoelectric conversion device and outputting the resulting integral value; a device for outputting a numerical value corresponding to a quantity of exposure light which is to be applied to the photographic plane; a device for converting the integral value into a numerical value on the same scale as that of the numerical value of the exposure quantity; and a device for deciding an exposure time by comparing the numerical value of the exposure quantity and the output value from the integral value converting device.

In addition, there is provided a photographing light quantity controller for an endoscope, which is used to control the quantity of illuminating light when a photograph is to be taken through the endoscope, comprising a device for supplying light for illuminating an object to the endoscope; a photoelectric conversion device for converting into an electric signal, a brightness level of exposure light that is applied to a photographic plane in a photographing device after being reflected from the object; a device for integrating the output from the photoelectric conversion device and outputting the resulting integral value; a device for outputting a numerical value corresponding to a quantity of exposure light which is to be applied to the photographic plane; a device for converting the integral value into a numerical value on the same scale as that of the numerical value of the exposure quantity; and a device for deciding an exposure time by comparing the numerical value of the exposure quantity and the output value from the integral state value converting device, and controlling the period of time for supplying illuminating light to the endoscope from the light source on the basis of the exposure time calculated.

BRIEF DESCRIPTION OF THE DRAWINGS

The present invention may be more fully understood from the description of a preferred embodiment of the invention set forth below, together with the accompanying drawings, in which:

FIGS. 3A and 3B are charts exemplarily showing numerical values of the converted exposure quantity in the embodiment;

DESCRIPTION OF THE EMBODIMENTS

Figure 1:
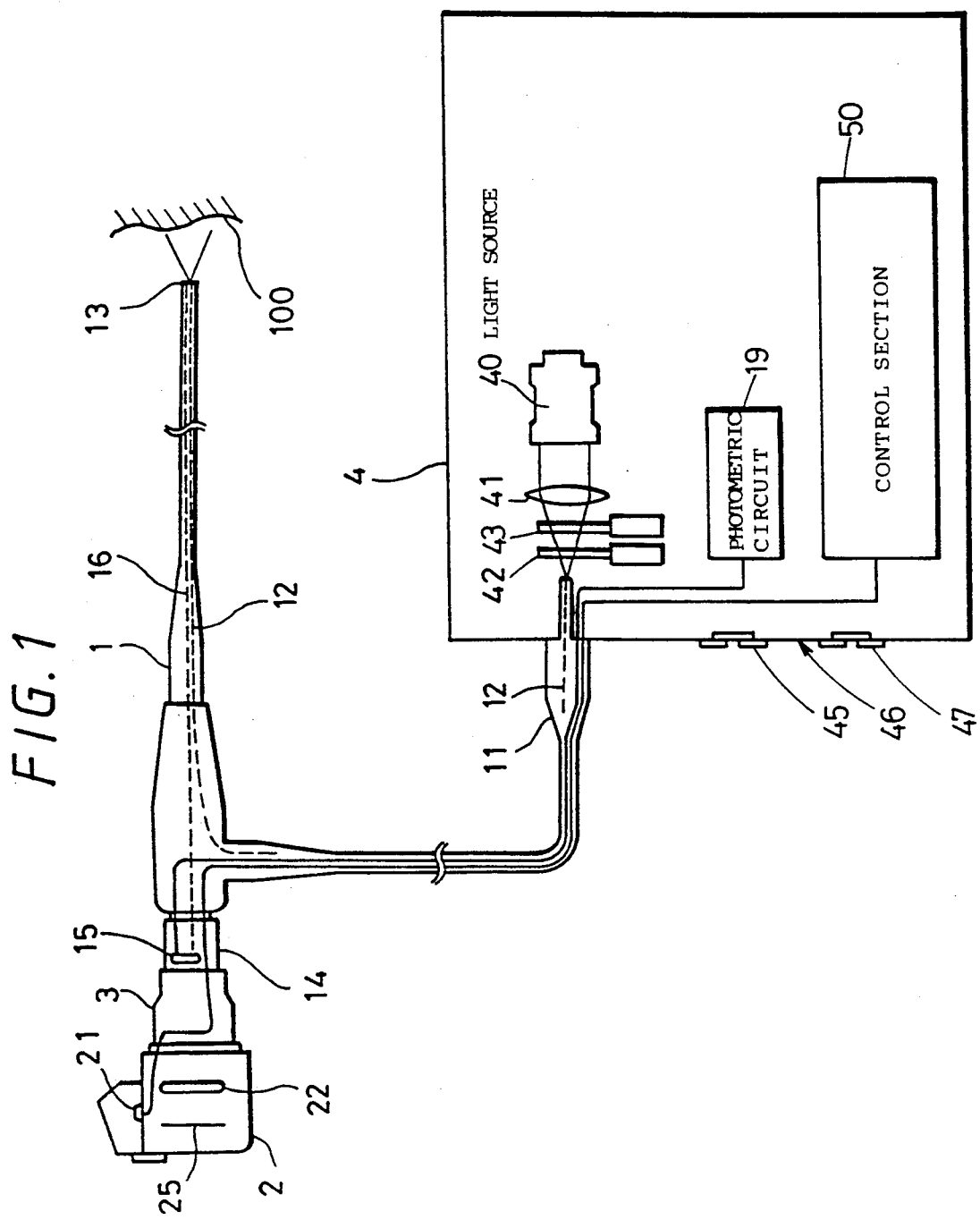
FIG. 1 is a schematic view showing the whole arrangement of one embodiment of the present invention.

Referring to FIG. 1, which shows the whole arrangement of one embodiment of the present invention, reference numeral 1 denotes an endoscope. A camera (photographing device) 2 is detachably attached to an eyepiece 14 of the endoscope 1 through a photographic adapter 3.

Reference numeral 4 denotes a light source apparatus, to which is detachably connected a connector 11 of the endoscope 1. Illuminating light that is emitted from a light source (lamp) 40 is condensed through a condenser lens 41 so as to be made incident on a light guide fiber bundle 12 in the endoscope 1.

In an illuminating light path, which extends between the light source 40 and the light guide fiber bundle 12, are provided a shutter (light source shutter) 42 which can be opened and closed to fully open and close the illuminating light path, and a variable diaphragm 43, which is capable of varying the area of passage of the illuminating light.

The illuminating light is transmitted through the light guide fiber bundle 12 and applied to an object 100 from the distal end 13 of an insert part of the endoscope 1. The reflected light from the object 100 is transmitted through an image guide fiber bundle 16 to expose the plane (photographic plane) of a film 25 in the camera 2. A shutter 22, in the camera 2, is opened for a predetermined time (e.g., 0.25 sec) only when a synchro switch 21 is turned on.

A light-receiving element 15 is provided in the eyepiece 14 to convert a brightness level of the exposure light, that is applied to the plane of the film 25, into an exposure quantities, i.e., various quantities of exposure light which is to be applied to the photographic plane 25, in the form of integer values obtained by conversion on a certain scale in advance (i.e., converted exposure quantities). In a photographing operation, an integer value, corresponding to an exposure quantity set by the exposure index setting switch 45, is read out from the ROM 53.

FIG. 3A shows the converted exposure quantity $V_I$ stored in the ROM 53 in comparison to the conventional reference voltage $V_R$. As shown in the FIGURE nine values for the converted exposure quantity $V_I$ are values which are all converted to integer values, with a standard being set at 128, for example.

It should be noted that the integer values (converted exposure quantities) do not necessarily need to be stored in the ROM 53. The arrangement may be such that a function, for calculating an integer value from an exposure index set by the exposure index setting switch 45, is stored in the ROM 53 to calculate a converted exposure quantity $V_I$ in the form of an integer value from the function in the CPU 51 for each photographing operation.

Assuming that the exposure quantity (relative value) is Q, the exposure index is EI and the converted exposure quantity is $V_I$ and that these factors are in relation with each other. For example, as shown in FIG. 3B, the converted exposure quantity VI can be obtained as follows:

$$V_I = 128 \times 2^{(10-EI)/2}$$

$$V_I = 128 \times Q$$

Referring back to FIG. 2, the system bus 52 is further connected with first to third input/output ports 56, 57 and 58. The exposure index setting switch 45 and the brightness setting switch 47 are connected to the input terminal of the first input/output port 56.

The output from the light-receiving element 15 is integrated in the photometric (integration) circuit 19 to obtain an integral value (integral output voltage V), which is inputted to a converter circuit 60.

The converter circuit 60 converts the input signal into a proper voltage, which is conformable to the input-output characteristics of an analog-to-digital converter 17. The input signal is outputted from the converter 17 in the form of an integer signal on the same scale as that of the converted exposure quantities stored in the ROM 53. Specifically, the converter circuit 60 is an amplifier circuit, for example. The output signal from the converter circuit 60 is inputted to a multiplexer 61 directly and via a sample-and-hold circuit 62.

More specifically, before the exposure is started, the peak value of the output signal from the converter circuit 60, that is sampled in the sample-and-hold circuit 62, is In the example shown in FIG. 3A, the scale is set such that an integer value of 128 ($V_I$) is outputted in correspondence to 1V ($V_R$). Therefore, the converter circuit 60 amplifies (converts) the integral output voltage from the photometric circuit 19, according to the following equation in advance:

$$V_I = a - 128 \times V/\overline{V_n} = 128 \times a \times V_n/N$$

where V is the integral output voltage from the photometric circuit 19, and a is a correction coefficient.

Thus, the integral state value outputted from the photometric circuit 19 is converted on the same scale as that of the converted exposure quantities stored in the ROM 53, on the whole.

It should be noted that the function of the converter circuit 60 may be realized by use of software.

A clock signal that is outputted from a timer 63 that is connected to the system bus 52 is inputted to a sampling circuit 64, so that a sampling pulse is outputted from the sampling circuit 64 to the photometric circuit 19 at a predetermined period in synchronism with the clock signal. During the observation, when the sampling pulse is at a low level, the photometric circuit 19 performs an integral operation, whereas, when the sampling pulse is at a high level, the integral output is zero (i.e., V=0). The sampling frequency is set, for example, at about 500 Hz, selected in the multiplexer 61 and inputted to the analog-to-digital conveter 17. Whereas, after the start of the exposure, the output signal from the converter circuit 60 itself is selected in the multiplexer 61 and inputted to the analog-to-digital converter 17.

The analog-to-digital converter 17 converts the input signal into an integer signal in accordance with predetermined input-output characteristics thereof and outputs it to the second input/output port 57.

The conversion characteristics of the converter circuit 60 will be explained below to clarify the meaning of the term "the same scale".

Figure 3C:
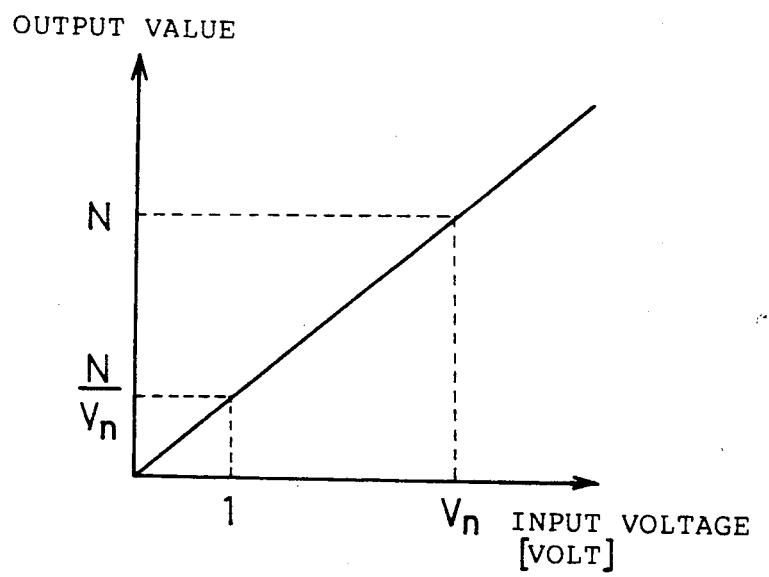
FIG. 3C is a reference drawing for explanation of the characteristics of a converter circuit in the embodiment.

It is assumed that the input-output characteristics of the analog-to-digital converter 17 are set to output an integer signal of 0 to N (N: a positive integer) in proportion to the input voltage of 0 to $V_n$ [volt], as shown in FIG. 3C. In other words, it is assumed that the analog-to-digital converter 17 outputs a numerical value of $N/V_n$ for an input signal of 1V, for example. If this ratio coincides with the ratio of $V_I/V_R$ in FIG. 3A, the integer signal outputted from the analog-to-digital converter 17 can be said to be on "the same scale" as that of the converted exposure quantitites. Whereas, if the two ratios are not coincident with each other, the input signal must be amplified in advance. electric signal. The output voltage from the light-receiving element 15 is integrated in a photometric (integration) circuit 19, and an integral state value is outputted from the photometric circuit 19. The photometric circuit 19 may be provided in either the light source apparatus 4 or the endoscope 1.

An exposure index setting switch 45 is provided on an operation panel 46, that is attached to the surface of the light source apparatus 4 to set an exposure index that determines a quantity of light, which is to be applied to the photographic plane 25 in the camera 2. A brightness setting switch 47 is used to set a brightness level of illuminating light that is supplied to the endoscope 1 when used in an observation state.

Reference numeral 50 denotes a control section which incorporates a central processing unit (CPU).

Figure 2:
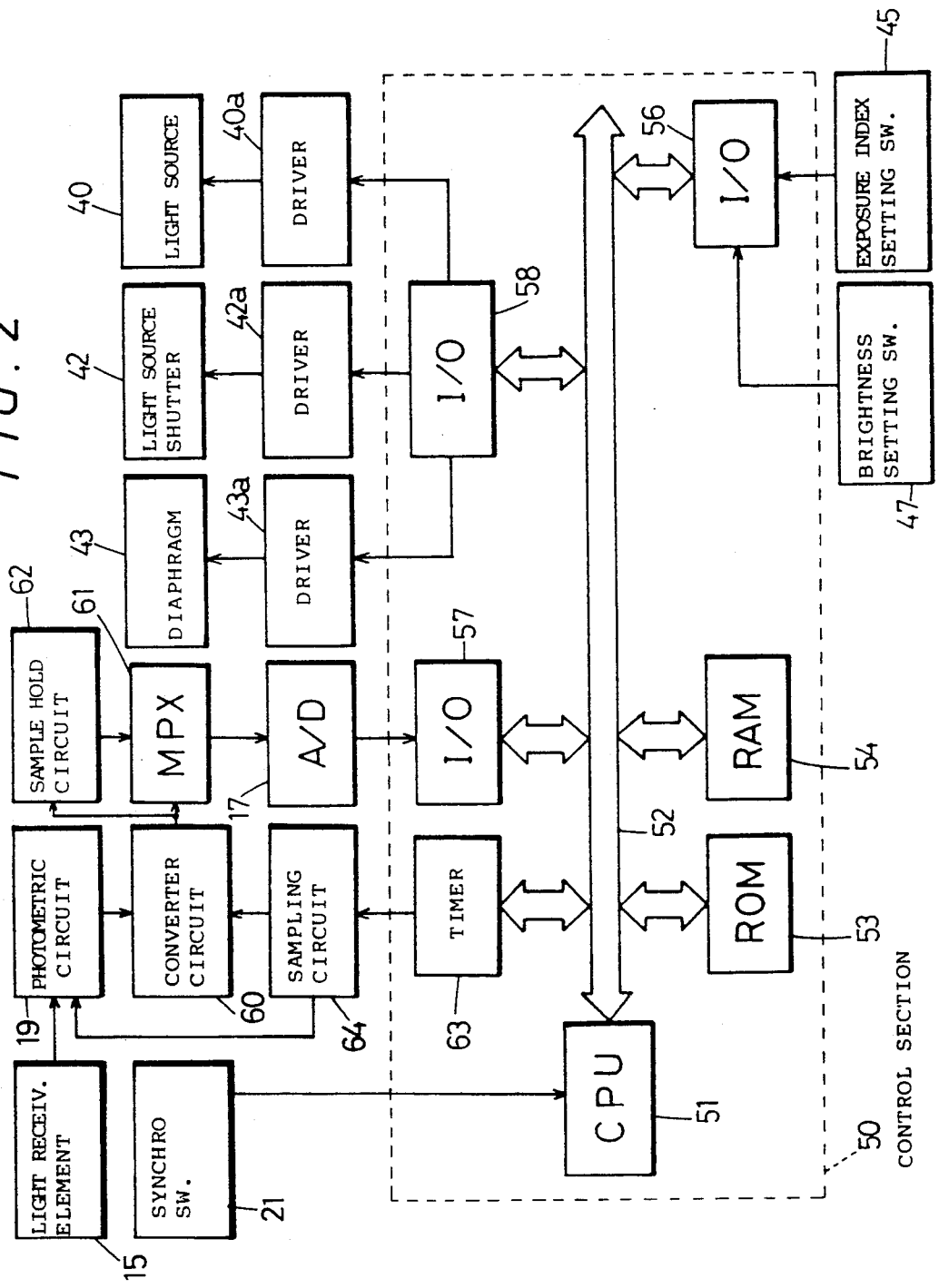
FIG. 2 is a circuit block diagram of the embodiment.

FIG. 2 is a block diagram showing the electrical arrangement of this embodiment. The control section 50 includes the CPU 51, and a read only memory (ROM) 53 and a random access memory (RAM) 54 both of which are connected to the CPU 51 through a system bus 52. The CPU 51 is supplied with an interrupt signal which is outputted from the synchro switch 21.

The ROM 53 is stored with software for controlling the operation of the CPU 51 and also with a plurality of data of that is, the integration time is shorter than the exposure time.

The output terminal of the third input/output port 58 is connected to drivers 40a, 42a and 43a which control the brightness of light that is emitted from the light source 40, the opening and closing operation of the light source shutter 42, and the degree of opening of the variable diaphragm 43, respectively.

Figure 4:
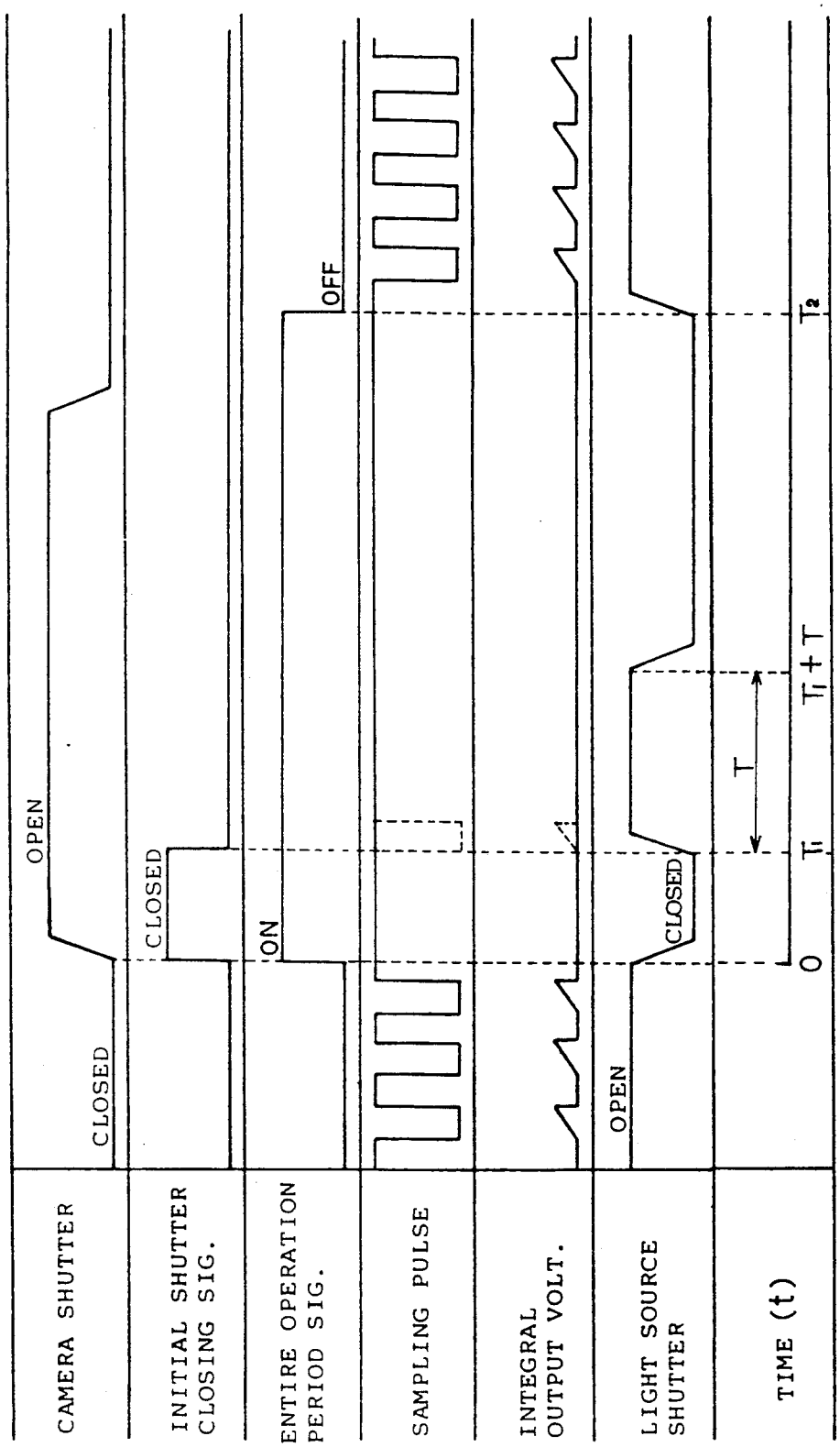
FIG. 4 is a time chart showing the operation of the embodiment.

FIG. 4 is a time chart showing the operation of this embodiment.

When the synchro switch 21 on the camera 2 is turned on, the shutter (camera shutter) 22 in the camera 2 is opened with a slight delay and is closed after a predetermined time (e.g., 0.25 sec) has elapsed. Meantime, the light source shutter 42 in the light source apparatus 4 is temporarily closed at the same time as the synchro switch 21 is turned on. After a predetermined short time (the initial shutter closing time $T_1$) has elapsed, the light source shutter 42 is opened again. The initial shutter closing time $T_1$ is, for example, 0.035 sec from the moment the synchro switch 21 is turned on.

Before the synchro switch 21 of the camera 2 is turned on, that is, during the observation, an illuminating light flux, that corresponds to a brightness level set through the brightness setting switch 47, is constantly supplied to the endoscope 1 from the light source apparatus 4. Every time the sampling pulse is at the low level, the output voltage from the light-receiving element 15 is integrated, and the peak value of the integral output voltage, that is sampled in the sample-and-hold circuit 62, is selected in the multiplexer 61 and inputted to the CPU 51.

When the exposure time T has elapsed due to the light source shutter 42 beginning to open, the light source shutter 42 is closed again. When the entire operation terminating period $T_2$ (e.g., 0.5 sec) has elapsed since the turning on of the synchro switch 21, all the elements of the system return to the previous state, i.e., the state before the turning on of the synchro switch 21. Thus, the light source shutter 42 opens again to provide an observation state.

Figure 5:
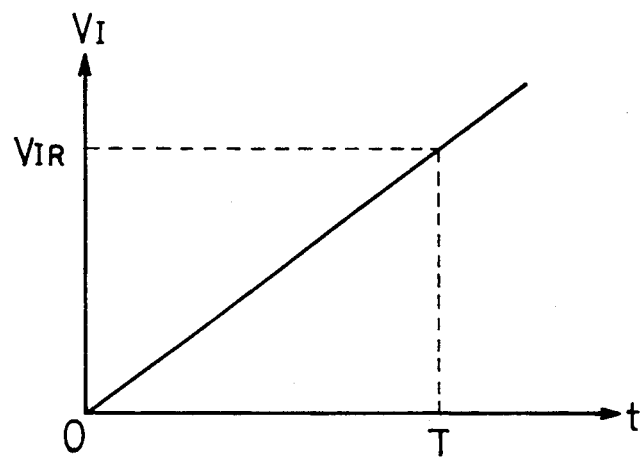
FIGS. 5 and 6 are graphs showing the way of obtaining the exposure time T in the embodiment.
Figure 6:
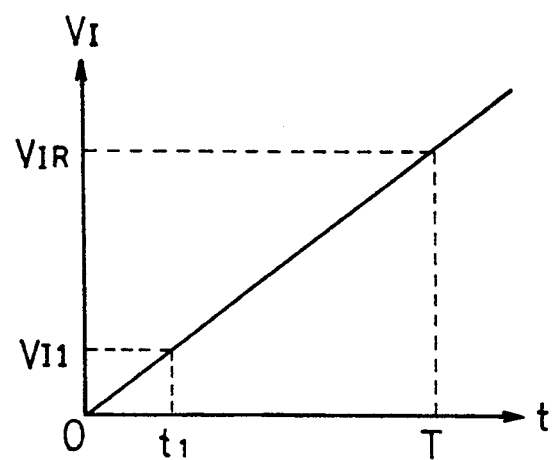

FIGS. 5 and 6 schematically illustrate one example of the way of obtaining the exposure time T.

Assuming that a numerical value, that is obtained by converting the integral output voltage V from the photometric circuit 19 on the same scale as that of the converted exposure quantity $V_I$ (in the converter circuit 60) is $V_T$ and the rate of change of $V_T$ per unit time is a (i.e., $a = dV_T/dt$), the exposure time T is calculated; for example, by $$T = V_I/a.$$

Accordingly, when $dV_T/dt(=a)$ is calculated before the light source shutter 42 is opened releasing the illuminating light for photographing, that is, before the plane of the film 25 in the camera 2 is exposed to light, the exposure time T is given by $T = V_{IR}/a$, as shown in FIG. 5, where $V_{IR}$ is a converted exposure quantity corresponding to the set exposure quantity $V_I$.

When $dV_T/dt(=a)$ is calculated after the light source shutter 42 has been opened to exposing the plane of the film 25 (i.e., after the time $t_1$ has elapsed), the exposure time T is given by $T - t_1 = (V_{IR} - V_{I1})$, as shown in FIG. 6, where $V_{I1}$ is a converted exposure quantity (integer value) corresponding to the quantity of exposure light applied until $t_1$ has elapsed.

Figure 7:
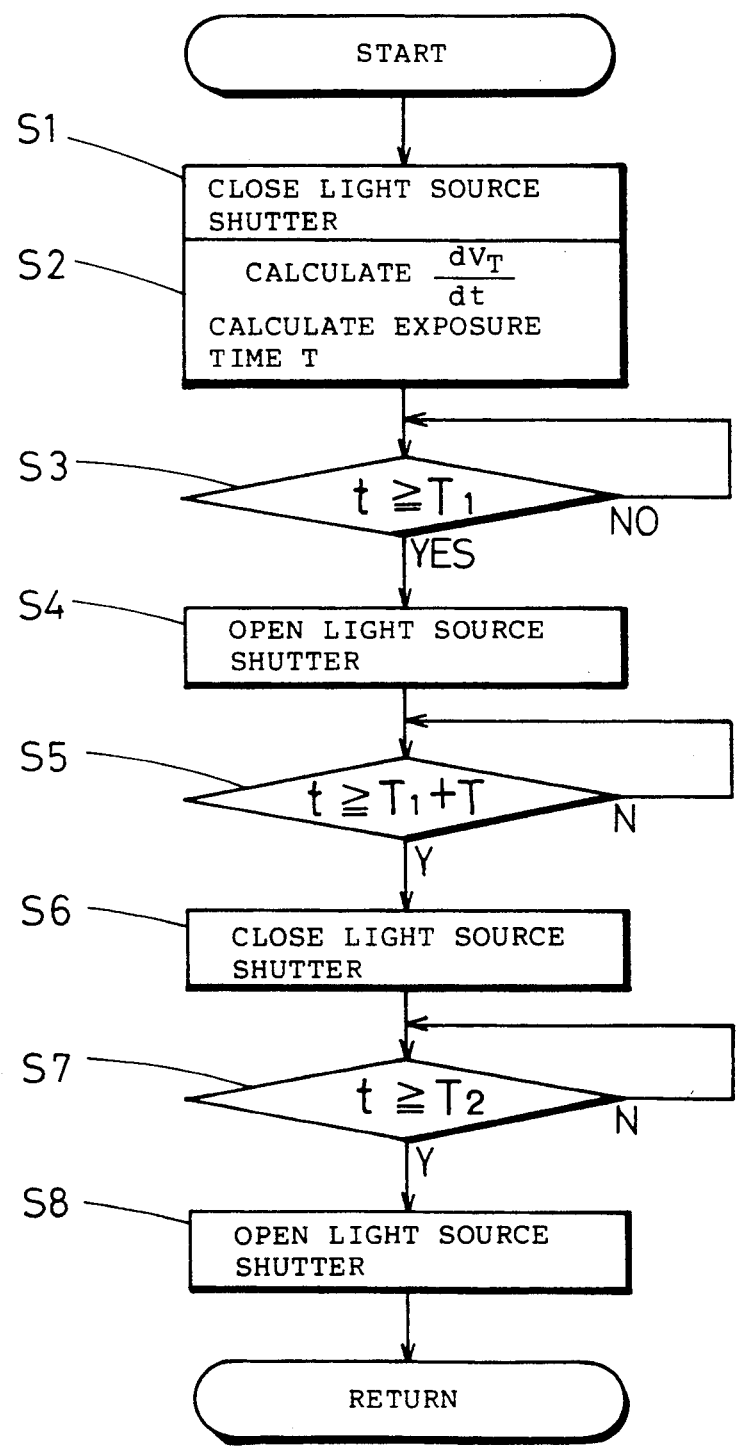
FIGS. 7 and 8 are flowcharts each showing a control process in the embodiment.

FIG. 7 is a flowchart showing a process that is executed by software to obtain $dV_T/dt(=a)$ before the light source shutter 42 is opened. In the FIGURE, S denotes Steps.

This process is initiated in response to an interrupt signal that is outputted when the synchro switch 21 is turned on. First, the light source shutter 42 is closed in S1. Then, $dV_T/dt(=a)$ is calculated and further an exposure time is calculated in S2.

When it is decided in S3 that the initial shutter closing time $T_1$ has elapsed, the light source shutter 42 is opened in S4. When it is decided in S5 that the exposure time T has elapsed since the light source shutter 42 began to open, the light source shutter 42 is closed in S6.

When it is decided in S7 that the entire operation terminating time $T_2$ has elapsed, the light source shutter 42 is opened in S8, thus completing the process.

Figure 8:
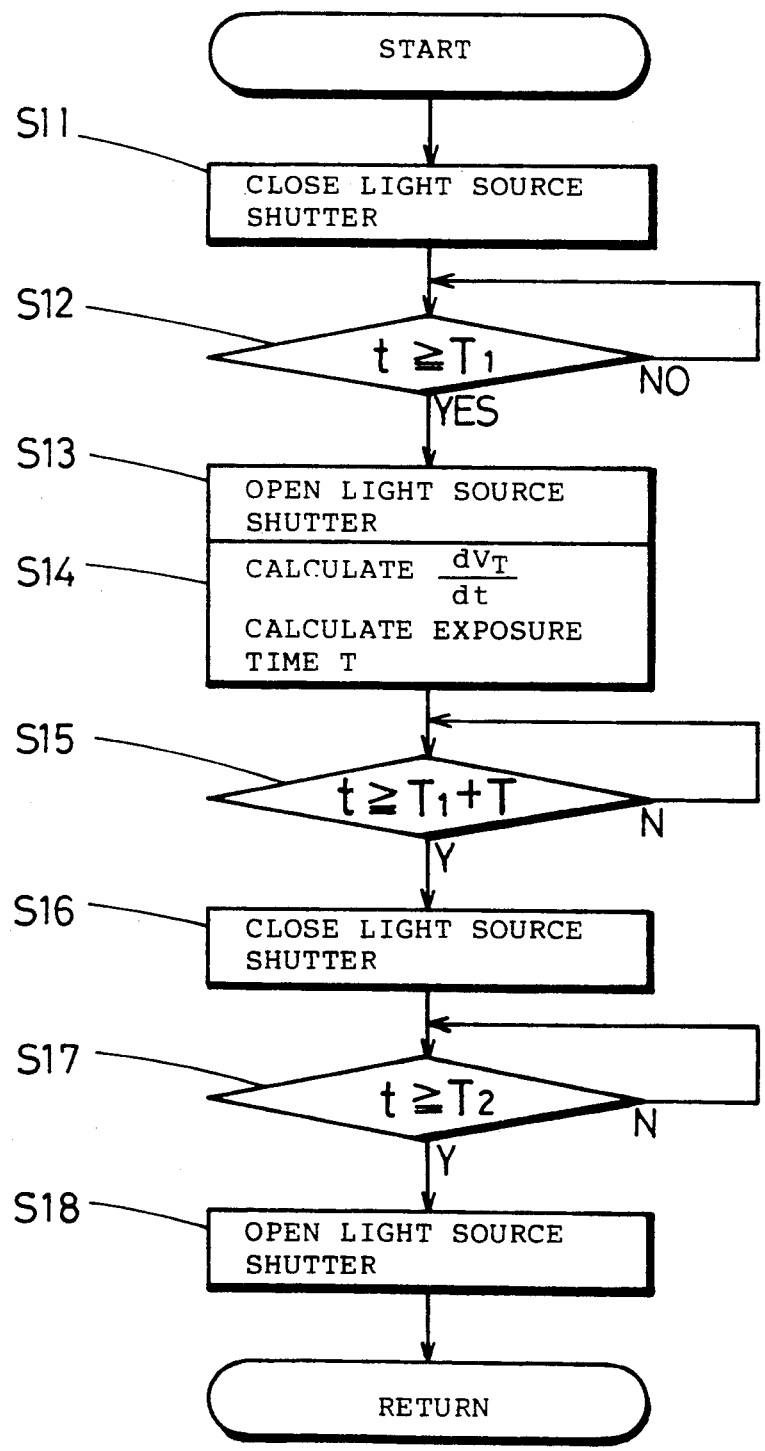

FIG. 8 is a flowchart showing a process that is executed by software to obtain $dV_T/dt(=a)$ after the light source shutter 42 has been opened. This flowchart differs from the flowchart of FIG. 7 only in the sequence of steps, that is, S2 in FIG. 7 comes next to S4, and in the content of calculation of the exposure time T, as stated above.

The point of the exposure control in this embodiment resides in the calculation of an accurate value for $dV_T/dt(=a)$.

Figure 9:
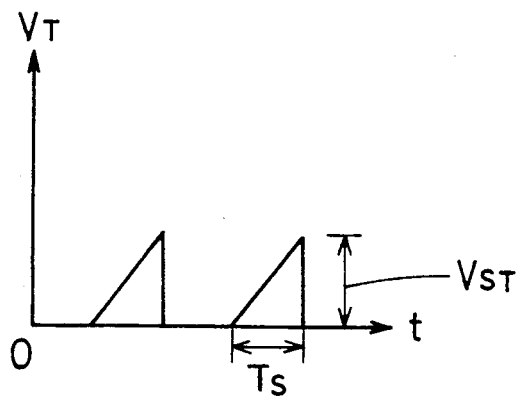
FIGS. 9 and 10 are graphs showing the way of obtaining a rate of change of $V_T$ per unit time in the embodiment.

(1) In the case where $dV_T/dt$ is calculated before the light source shutter is opened:

A peak value $V_S$ of the integral output voltage, sampled by the sampling pulse immediately before the photographing operation is initiated, is employed. If an integer value, that is obtained by converting the peak value $V_S$ on the same scale as that of the converted exposure quantity $V_I$, is represented by $V_{ST}$, as shown in FIG. 9, $dV_T/dt(=a)$ is given by $$a = dV_T/dt = b \cdot V_{ST}/T_S$$

where $T_S$ is a sampling time, that is, a time the sampling pulse is low level, and b is the ratio of the value fe of the diaphragm 43 in the light source apparatus 4 during a photographing operation to the value fs immediately before the photographing operation is initiated (i.e., b=fe/fs).

It should be noted that both fe and fs are greater than 0 and not greater than 1 and express a rate at which the flux of light passes through the diaphragm 43.

(2) In the case where $dV_T/dt$ is calculated after the light source shutter has been opened:

Considering that the range of the integral output voltage V is wide, the value for $\Delta t$ in $dV_T/dt = C \cdot \Delta V_T/\Delta t$ is varied to calculate $dV_T/dt (=a)$. C is a correction coefficient.

Figure 10:
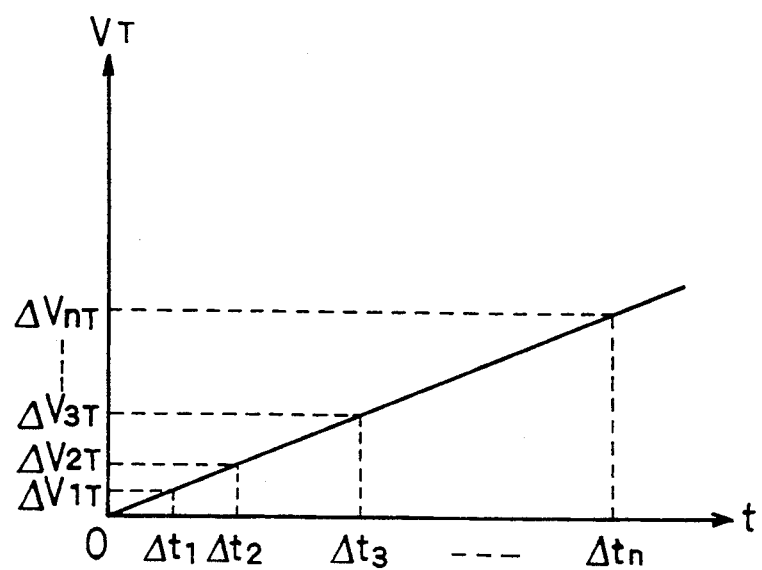
Figure 11:
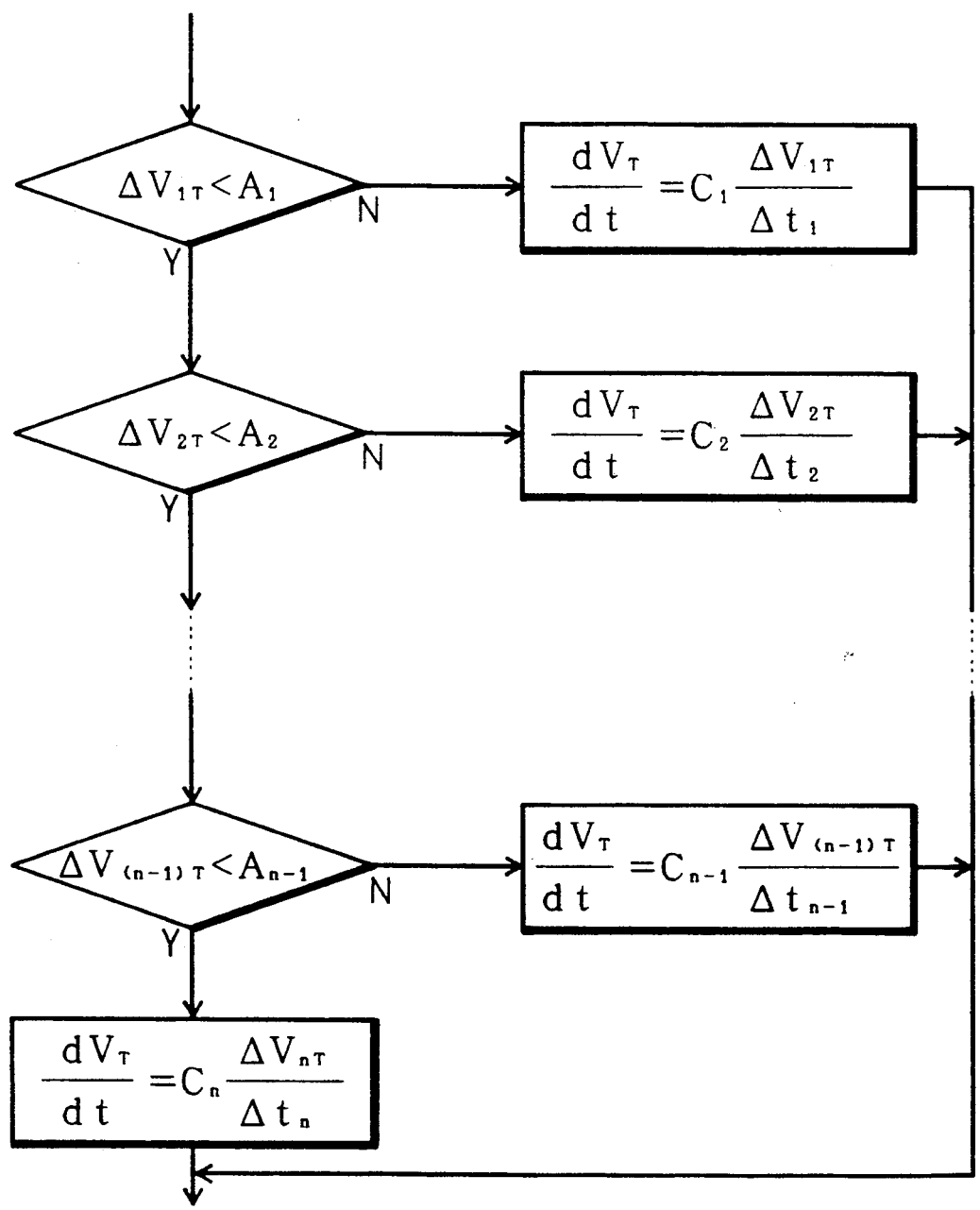
FIG. 11 is a flowchart showing an operation of obtaining a rate of change of $V_T$ per unit time in the embodiment.

More specifically, assuming that $\Delta t$ is $\Delta t_1 < \Delta t_2 < \ldots \Delta t_n$ and that $\Delta V_T$ corresponding to these values for $\Delta t$ are $\Delta V_{1T}, \Delta V_{2T}, \ldots, \Delta V_{nT}$, as shown in FIG. 10, $\Delta V_T$ is compared with A successively in the mentioned order, and $dV_T/dt$ is calculated from $C \cdot \Delta V_T/\Delta t$ at the time when $\Delta V_T < A$ becomes invalid, as shown exemplarily in the flowchart of FIG. 11.

In FIG. 11, $A_1, A_2 \ldots$ are certain constants that limit the greatest lower bound of $\Delta V$ and may be set to be $A_1 = A_2 = \ldots = A_{n-1}$.

$C_1, C_2, \ldots C_n$ are correction coefficients, which are normally set to be $C_1 > C_2 > \ldots > C_n \geq 1$.

Although in the foregoing embodiment the converted exposure quantities are integral values, it should be noted that the present invention is not necessarily limited thereto and that proper numerical values may be employed as converted exposure quantities.

According to the present invention, setting of an exposure quantity can be effected by use of a mere numerical value without the need to employ a reference voltage. Accordingly, it becomes unnecessary to employ a power supply circuit for producing a reference voltage, so that the hardware for setting an exposure quantity is simplified considerably and the cost of the product can be lowered by a large margin in comparison to the prior art.

While the invention has been described by reference to a specific embodiment chosen for purposes of illustration, it should be apparent that numerous modifications could be made thereto by those skilled in the art without departing from the basic concept and scope of the invention.

We claim:

1. A photographing light quantity controller for an endoscope, which is used to control the quantity of illuminating light when a photograph is to be taken through said endoscope, comprising:
   means for supplying light for illuminating an object to be viewed by said endoscope;
   photoelectric conversion means for converting into an electric signal, a brightness level of exposure light that is applied to a photographic plane in a photographing device after being reflected from said object;
   means for integrating output from said photoelectric conversion means and outputting a resulting integral value;
   means for outputting a numerical value corresponding to a quantity of exposure light which is to be applied to said photographic plane;
   means for converting said integral value into a numerical value on a same scale as that of said numerical value of exposure quantity; and
   means for deciding an exposure time by comparing said numerical value of the exposure quantity and an output value from said integral state value converting means.

2. A photographing light quantity controller for an endoscope according to claim 1, wherein the numerical value of said integral state valve converting means, is a whole number value.

3. A photographing light quantity controller for an endoscope according to claim 1, wherein said outputting means is stored with a plurality of exposure quantities, respectively, corresponding to different exposure indexes in the form of numerical values obtained by conversion.

4. A photographing light quantity controller for an endoscope according to claim 1, wherein said outputting means is a read only memory.

5. A photographing light quantity controller for an endoscope according to claim 1, wherein said integral value converting means is a central processing unit (CPU).

6. A photographing light quantity controller for an endoscope according to claim 1, wherein said integrating means integrates the output from said photoelectric conversion means at a predetermined period which is shorter than the exposure time.

7. A photographing light quantity controller for an endoscope according to claim 6, wherein the integration by said integrating means is carried out before exposure light is applied to said photographic plane in said photographing device.

8. A photographing light quantity controller for an endoscope according to claim 1, wherein the integration by said integrating means is carried out while exposure light is being applied to said photographic plane in said photographing device.

9. A photographing light quantity controller for an endoscope, which is used to control the quantity of illuminating light when a photograph is to be taken through said endoscope, comprising:
   means for supplying light for illuminating an object to be view by said endoscope;
   photoelectric conversion means for converting into an electric signal, a brightness level of exposure light that is applied to a photographic plane in a photographing device after being reflected from said object;
   means for integrating a output from said photoelectric conversion means and outputting a resulting integral value;
   means for outputting a numerical value corresponding to a quantity of exposure light which is to be applied to said photographic plane;
   means for converting said integral state value into a numerical value on a same scale as that of said numerical value of the exposure quantity and outputting said numerical value; and
   means for deciding an exposure time by comparing a numerical value of the exposure quantity and an output value from said integral value converting means and controlling the period of time for supplying illuminating light to said endoscope from said light source on the basis of the exposure time calculated.

10. A photographing light quantity controller for an endoscope according to claim 9, wherein said numerical value obtained by said outputting means is a whole number value.

11. A photographing light quantity controller for an endoscope according to claim 9, wherein said integrating means integrates the output from said photoelectric conversion means at a predetermined period which is shorter than the exposure time.

12. A photographing light quantity controller for an endoscope according to claim 11, wherein the integration by said integrating means is carried out before exposure light is applied to the photographic plane in said photographing device.

13. A photographing light quantity controller for an endoscope according to claim 9, wherein the integration by said integrating means is carried out while exposure light is being applied to the photographic plane in said photographing device.

* * * * *

UNITED STATES PATENT AND TRADEMARK OFFICE
CERTIFICATE OF CORRECTION

PATENT NO. : 5,159,380
DATED : October 27, 1992
INVENTOR(S) : K. FURUYA et al.

It is certified that error appears in the above-indentified patent and that said Letters Patent is hereby corrected as shown below:

At column 7, line 67 (claim 1, line 23) delete "state".
At column 8, line 3 (claim 2, line 3) change "state valve" to ---value---.
At column 8, line 38 (claim 9, line 6) change "view" to ---viewed---.
At column 8, line 50 (claim 9, line 18) delete "state".

Signed and Sealed this

Third Day of May, 1994

Attest:

BRUCE LEHMAN

Attesting Officer       Commissioner of Patents and Trademarks